(12) United States Patent
Azhar et al.

(10) Patent No.: US 12,372,520 B2
(45) Date of Patent: *Jul. 29, 2025

(54) METHOD, DEVICE AND SYSTEM FOR DETERMINING THE CONCENTRATION OF ANALYTES IN A SAMPLE

(71) Applicant: Siemens Healthcare Diagnostics Inc., Tarrytown, NY (US)

(72) Inventors: Mohiudeen Azhar, Bangalore (IN); Kalpesh Mehta, Singapore (SG); Ragavendar Ms, Flanders, NJ (US); Sudipa Galgalkar, Bangalore (IN); Ishita Chakraborty, Bangalore (IN)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 880 days.

This patent is subject to a terminal disclaimer.

(21) Appl. No.: 17/264,529

(22) PCT Filed: Jul. 31, 2019

(86) PCT No.: PCT/US2019/044307
§ 371 (c)(1),
(2) Date: Jan. 29, 2021

(87) PCT Pub. No.: WO2020/033194
PCT Pub. Date: Feb. 13, 2020

(65) Prior Publication Data
US 2021/0293803 A1 Sep. 23, 2021

Related U.S. Application Data

(60) Provisional application No. 62/715,026, filed on Aug. 6, 2018.

(51) Int. Cl.
*G01N 33/72* (2006.01)
*G01N 21/31* (2006.01)
*G01N 33/543* (2006.01)

(52) U.S. Cl.
CPC ....... *G01N 33/54373* (2013.01); *G01N 21/31* (2013.01); *G01N 33/72* (2013.01); *G01N 2021/3133* (2013.01)

(58) Field of Classification Search
CPC .. G01N 33/54373; G01N 21/31; G01N 33/72; G01N 2021/3133; G01N 33/49
See application file for complete search history.

(56) References Cited

U.S. PATENT DOCUMENTS 6,235,536 B1 * 5/2001 Wardlaw ............ G01N 33/5002
436/805
6,819,408 B1 11/2004 Scrivens et al.
(Continued)

FOREIGN PATENT DOCUMENTS

EP           2793015 A1 * 10/2014 ........... A61B 5/1455
WO   WO-2016115014 A1 *  7/2016 ........ B01L 3/502715
WO   WO-2017085180 A1 *  5/2017 ........ B01L 3/502715

OTHER PUBLICATIONS

International Search Report and Written Opinion of International Application No. PCT/US2019/044307 dated Oct. 29, 2019.
(Continued)

*Primary Examiner* — Said M Elnoubi (57) ABSTRACT

A method, device and a system of determining a concentration of one or more analytes in a sample is disclosed. In one aspect of the invention, the method includes introducing the sample through a channel. The method further includes
(Continued)

illuminating the sample with light having varying wavelengths. Additionally, the method includes obtaining an image of the illuminated sample at each of the wavelengths. Furthermore, the method includes analyzing the image to determine the concentration of the one or more analytes.

6 Claims, 10 Drawing Sheets

(56) References Cited

U.S. PATENT DOCUMENTS

| | | | |
|---|---|---|---|
| 8,501,015 | B2 | 8/2013 | Fletcher et al. |
| 2012/0309636 | A1 | 12/2012 | Gibbons et al. |
| 2015/0044780 | A1* | 2/2015 | Kurz .................. G01N 33/6827 702/85 |
| 2017/0191982 | A1* | 7/2017 | Shatova ............ B01L 3/502746 |
| 2018/0106720 | A1 | 4/2018 | Schonbrun et al. |

OTHER PUBLICATIONS

Davis et al., "Deterministic hydrodynamics: Taking blood apart", PNAS, Oct. 3, 2006, vol. 103, No. 40, pp. 14779-14784.

Maria et al., "Capillary flow of blood in a microchannel with differential wetting for blood plasma separation and on-chip glucose detection", Biomicrofluidics, Sep. 2016, 10(5), pp. 1-15.

Homsy et al., "Development and Validation of a Low Cost Blood Filtration Element Separating Plasma from Undiluted Whole Blood", Biomicrofluidics, Mar. 2012, 6(1), pp. 1-9.

Tripathi et al., "Microdevice for plasma separation from whole human blood using biophysical and geometrical effects", Scientific Reports 6, Article No. 26749, Jun. 2016, pp. 1-15.

Chen et al., "Microfluidic chip for plasma separation from undiluted human whole blood samples using low voltage contactless dielectrophoresis and capillary force", Lab Chip, 2014, vol. 14, No. 12, pp. 1-7.

Haeberle et al., "Centrifugal extraction of plasma from whole blood on a rotating disk", Lab Chip, 2006, 6, pp. 776-781.

Lenshof et al., "Acoustic whole blood plasmapheresis chip for prostate specific antigen microarray diagnostics", Analytical Chemisty, Aug. 1, 2009, vol. 81, No. 15, pp. 6030-6037.

European Search Report and Written Opinion of European Application No. 19848137.6 dated Sep. 3, 2021.

Mauk et al., "Integrated Microfluidic Nucleic Acid Isolation, Isothermal Amplification, and Amplicon Quantification", Microassays, Oct. 20, 2015, vol. 4; pp. 474-489.

Crowley et al., "Isolation of plasma from whole blood using planer microfilters from lab-on-a-chip applications", Jul. 19, 2005 (Jul. 19, 2005), Lab On a Chip; vol. 5, No. 9, pp. 922-929.

Durc et al, "Fast blood plasma separation device for point-of-care applications", Feb. 8, 2018 (Feb. 8, 2018), Talanta; vol. 183, pp. 55-60.

\* cited by examiner

▲ Desired concentration of Hb: 200 mg/dL
■ Desired concentration of Hb: 100 mg/dL
○ Desired concentration of Hb: 50 mg/dL

1102

▲ Desired concentration of bilirubin: 20 mg/dL
■ Desired concentration of bilirubin: 10 mg/dL
○ Desired concentration of bilirubin: 5 mg/dL

1103

▲ Desired concentration of lipid: 600mg/dL
■ Desired concentration of lipid: 400mg/dL
○ Desired concentration of lipid: 200mg/dL

METHOD, DEVICE AND SYSTEM FOR DETERMINING THE CONCENTRATION OF ANALYTES IN A SAMPLE

The subject application claims benefit under 35 USC § 119(e) of U.S. provisional Application No. 62/715,026, filed Aug. 6, 2018. The entire contents of the above-referenced patent application are hereby expressly incorporated herein by reference.

FIELD OF TECHNOLOGY

The present disclosure relates to the field of analysis of a sample and more particularly to the field of determining the concentration of analytes in the sample.

BACKGROUND

Hemolysis is a phenomenon wherein the red blood cells rupture in whole blood, releasing their content into the blood plasma. This condition may occur due to various reasons such as immune reactions, infections, and medications. Hemolysis may occur within the body of an individual or after the blood has been drawn out of the body. A major cause of hemolysis is the pre-analytical steps involved in blood sample handling, including collection of the blood sample from an individual. Hemolysis alters the composition of the blood plasma due to the presence of degradation products of blood cells. If the composition of the blood plasma is altered beyond a certain threshold for hemoglobin and bilirubin, the blood sample is flagged for hemolysis. In such cases, the blood sample may become incapable of further usage and therefore has to be rejected. Therefore, the object of the invention is to provide a method to determine concentration of analytes, particularly free hemoglobin, in a whole blood sample. Free hemoglobin can cause interference while measuring levels of one or more analytes in blood. The object of the invention is achieved by a method and a device for determining the concentration of analytes in whole blood.

SUMMARY

A method of determining a concentration of one or more analytes in a sample is disclosed. In one aspect of the invention, the method includes introducing the sample through a channel. Additionally, the method includes illuminating the sample with light having varying wavelengths. Furthermore, the method includes obtaining an image of the illuminated sample at each of the wavelengths. The method also includes analyzing the image to determine the concentration of the one or more analytes.

In another aspect, a system for determining the concentration of one or more analytes in a sample includes a channel configured to carry the sample. The device further includes a light source configured to emit light at varying wavelengths, wherein the sample in the channel is illuminated at varying wavelengths using the light source. Additionally, the system includes a processing unit, a calibration database coupled to the processing unit and a memory coupled to the processing unit. The memory includes an image processing module configured for obtaining an image of the illuminated sample. The image processing module is further configured for analyzing the image to detect a cell-free plasma layer. Additionally, the image processing module is configured for determining the concentration of the one or more analytes in the cell-free plasma layer In another aspect, a device for determining the concentration of one or more analytes in a sample includes a channel configured to carry the sample. The device further includes a light source configured to emit light at varying wavelengths, wherein the sample is illuminated with light at varying wavelengths using the light source. Additionally, the device includes an imaging capturing module configured to capture an image of the illuminated sample.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present invention is further described hereinafter with reference to illustrated embodiments shown in the accompanying drawings, in which.

DETAILED DESCRIPTION

Hereinafter, embodiments for carrying out the present invention are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

Figure 1:
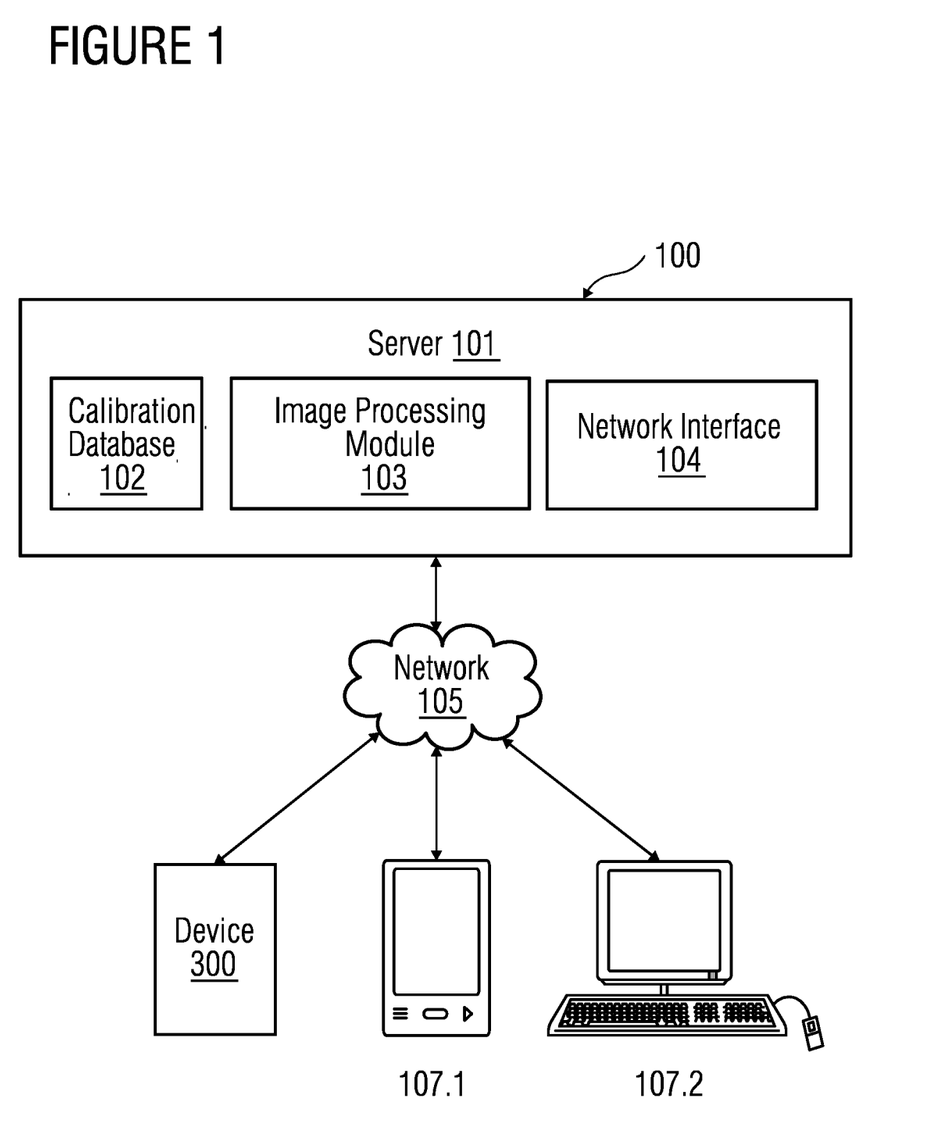
FIG. 1 illustrates block diagram of a client-server architecture which provides geometric modeling of components representing different parts of a real world object, according to an embodiment.

FIG. 1 provides an illustration of a block diagram of a client-server architecture that is a geometric modelling of components representing different parts of real-world objects, according to an embodiment. The client-server architecture 100 includes a server 101 and a plurality of client devices 107.1-107.2. Each of the client devices 107.1-107.2 is connected to the server 101 via a network 106, for example, local area network (LAN), wide area network (WAN), WiFi, etc. In one embodiment, the server 101 is deployed in a cloud computing environment. As used herein, "cloud computing environment" refers to a processing environment comprising configurable computing physical and logical resources, for example, networks, servers, storage, applications, services, etc., and data distributed over the network 106, for example, the internet. The cloud computing environment provides on-demand network access to a shared pool of the configurable computing physical and logical resources. The server 101 may include a calibration database 102 that comprises captured images of a channel comprising whole blood. The server 101 may include an image processing module 103 that analyzes the image of the whole blood to determine a concentration of one or more analytes. Additionally, the server 101 may include a network interface 104 for communicating with the client devices 107.1-107.2 via the network 105.

The client devices 107.1-107.n include a device 107.1 to determine the concentration of one or more analytes in the whole blood sample. The device 107.1 may be configured to capture an image of a processed whole blood sample. Such image may be sent to the server 101 via a network interface. The client devices 1017.1-107.n also include a user device 107.2, used by a user. In an embodiment, the user device 107.2 may be used by the user, to receive the concentration values of the one or more analytes present in the sample. The concentration values can be accessed by the user via a graphical user interface of an end user web application on the user device 107.n. In another embodiment, a request may be sent to the server 101 to access the concentration values via the network 106.

Figure 2:
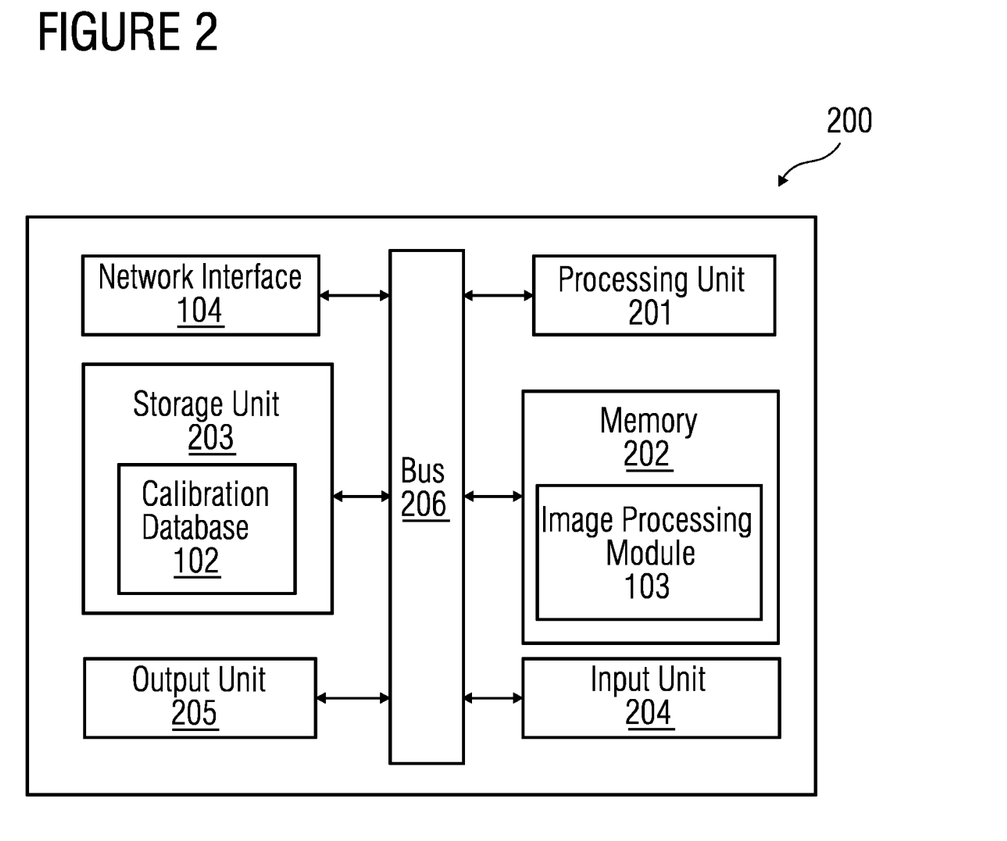
FIG. 2 illustrates a block diagram of a system in which an embodiment of a method of determining a concentration of one or more analytes in a sample can be implemented.

FIG. 2 is a block diagram of a system 101 in which an embodiment can be implemented, for example, as a system to determine the concentration of one or more analytes, configured to perform the processes as described therein. It is appreciated that the server 101 is an exemplary implementation of the system in FIG. 2. In FIG. 2, the system 101 comprises a processing unit 201, a memory 202, a storage unit 203, an input unit 204, an output unit 205 a network interface 105 and a standard interface or bus 206. The system 101 can be a (personal) computer, a workstation, a virtual machine running on host hardware, a microcontroller, or an integrated circuit. As an alternative, the system 101 can be a real or a virtual group of computers (the technical term for a real group of computers is "cluster", the technical term for a virtual group of computers is "cloud").

The processing unit 201, as used herein, means any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 201 may also include embedded controllers, such as generic or programmable logic devices or arrays, application specific integrated circuits, single-chip computers, and the like. In general, a processing unit 201 can comprise hardware elements and software elements. The processing unit 201 can be configured for multithreading, i.e. the processing unit 201 can host different calculation processes at the same time, executing the either in parallel or switching between active and passive calculation processes.

The memory 202 may be volatile memory and non-volatile memory. The memory 202 may be coupled for communication with the processing unit 201. The processing unit 201 may execute instructions and/or code stored in the memory 202. A variety of computer-readable storage media may be stored in and accessed from the memory 202. The memory 202 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 202 includes an image processing module 103 stored in the form of machine-readable instructions on any of the above-mentioned storage media and may be in communication to and executed by processing unit 201. When executed by the processing unit 201, the image processing module 103 causes the processing unit 201 to analyze the image of the sample to determine the concentration of one or more analytes. Method steps executed by the processing unit 201 to achieve the above-mentioned functionality are elaborated upon in detail in FIGS. 4, 5, and 6.

The storage unit 203 may be a non-transitory storage medium which stores a calibration database 102. The calibration database 102 is a repository of images associated with the whole blood in a channel 306. The input unit 204 may include input means such as keypad, touch-sensitive display, camera, etc. capable of receiving input signal. The bus 207 acts as interconnect between the processing unit 201, the memory 202, the storage unit 203, the communication interface 107 the input unit 204 and the output unit 205.

Those of ordinary skilled in the art will appreciate that the hardware depicted in FIG. 2 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, input/output (I/O) adapter, network connectivity devices also may be used in addition or in place of the hardware depicted. The depicted example is provided for the purpose of explanation only and is not meant to imply architectural limitations with respect to the present disclosure.

A system in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through the pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Washington may be employed if suitably modified. The operating system is modified or created in accordance with the present disclosure as described.

The present invention is not limited to a particular computer system platform, processing unit, operating system, or network. One or more aspects of the present invention may be distributed among one or more computer systems, for example, servers configured to provide one or more services to one or more client computers, or to perform a complete task in a distributed system. For example, one or more aspects of the present invention may be performed on a client-server system that comprises components distributed among one or more server systems that perform multiple functions according to various embodiments. These components comprise, for example, executable, intermediate, or interpreted code, which communicate over a network using a communication protocol. The present invention is not limited to be executable on any particular system or group of systems, and is not limited to any particular distributed architecture, network, or communication protocol.

Disclosed embodiments provide systems and methods for analyzing a sample. In particular, the systems and methods may determine a concentration of one or more analytes in a whole blood sample.

Figure 3:
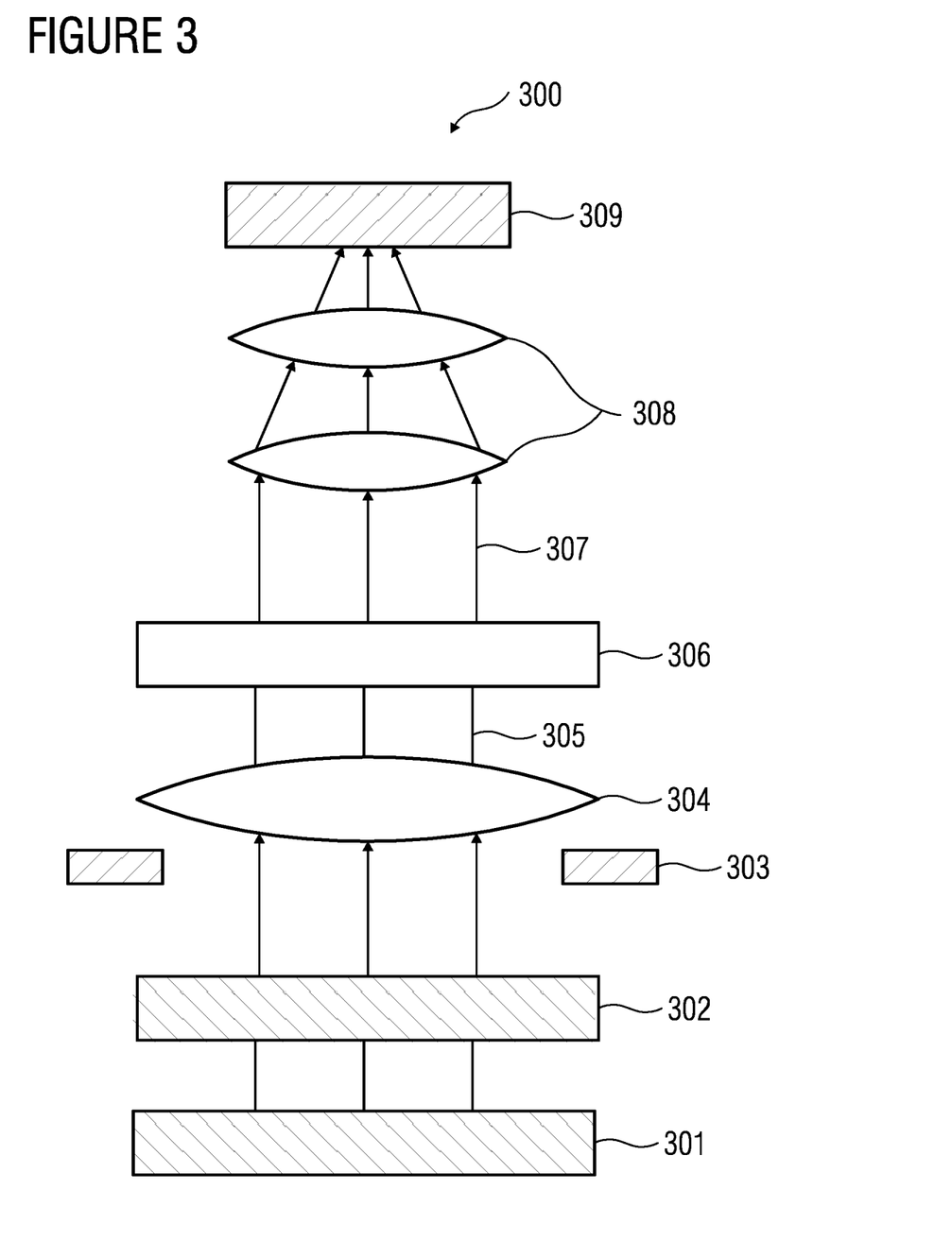
FIG. 3 illustrates an embodiment of a device for determination of a concentration of one or more analytes in the sample.

FIG. 3 illustrates an embodiment of a device 300 for determining the concentration of one or more analytes in the whole blood. The device 300 includes a light source 301. The light source 301 may be a multi-wavelength light source, i.e. capable of emitting light of varying wavelengths. In an embodiment, the light source 301 is configured to emit light of at least three different wavelength ranges. The wavelength ranges of the light source 301 may be, for example, between 400 nm and 420 nm; 440 nm and 460 nm; and 520 nm and 650 nm. The wavelength ranges may be defined based on an absorption peak for each analyte to be determined. In an embodiment, the light emitted 305 from the light source 301 may be homogenized using a diffuser 302. The device 301 further includes a channel 306 configured to carry the whole blood sample. The channel 306 may be, for example, a microfluidic channel 306 or a microfluidic chip. The microfluidic channel 306 may have a depth in the range between 100 and 200 μm. Therefore, the path length of the light in the channel 306 is low. The channel 306 may be transparent so as to allow light from the light source 301 to interact with the whole blood and is transmitted out 307. The light 305 from the light source 301 radiates on to the microfluidic channel 306 after passing through an iris 303 and a collimating lens 304. The device 300 additionally includes an imaging capturing module. The image capturing module may include imaging lenses 308 and an imaging sensor 309, configured to capture an image of the illuminated microfluidic channel 306. The imaging sensor 309 may be, for example a charge-coupled device (CCD) or a complementary metal oxide semiconductor (CMOS). In an embodiment, the image processing module is also configured to transfer the captured image to the server 101 for further processing. In another embodiment, the image capturing module is an exemplary embodiment of the input unit 204 in FIG. 2.

Figure 4:
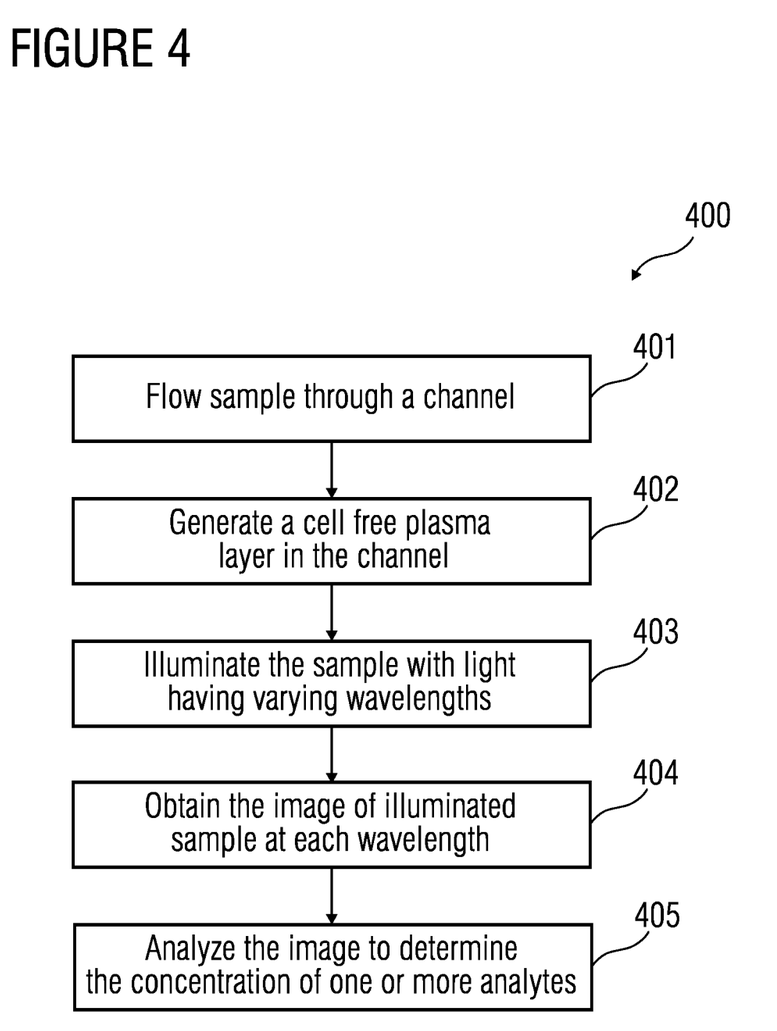
FIG. 4 illustrates a flowchart of an embodiment of a method of determining a concentration of one or more analytes in a sample.
Figure 7:
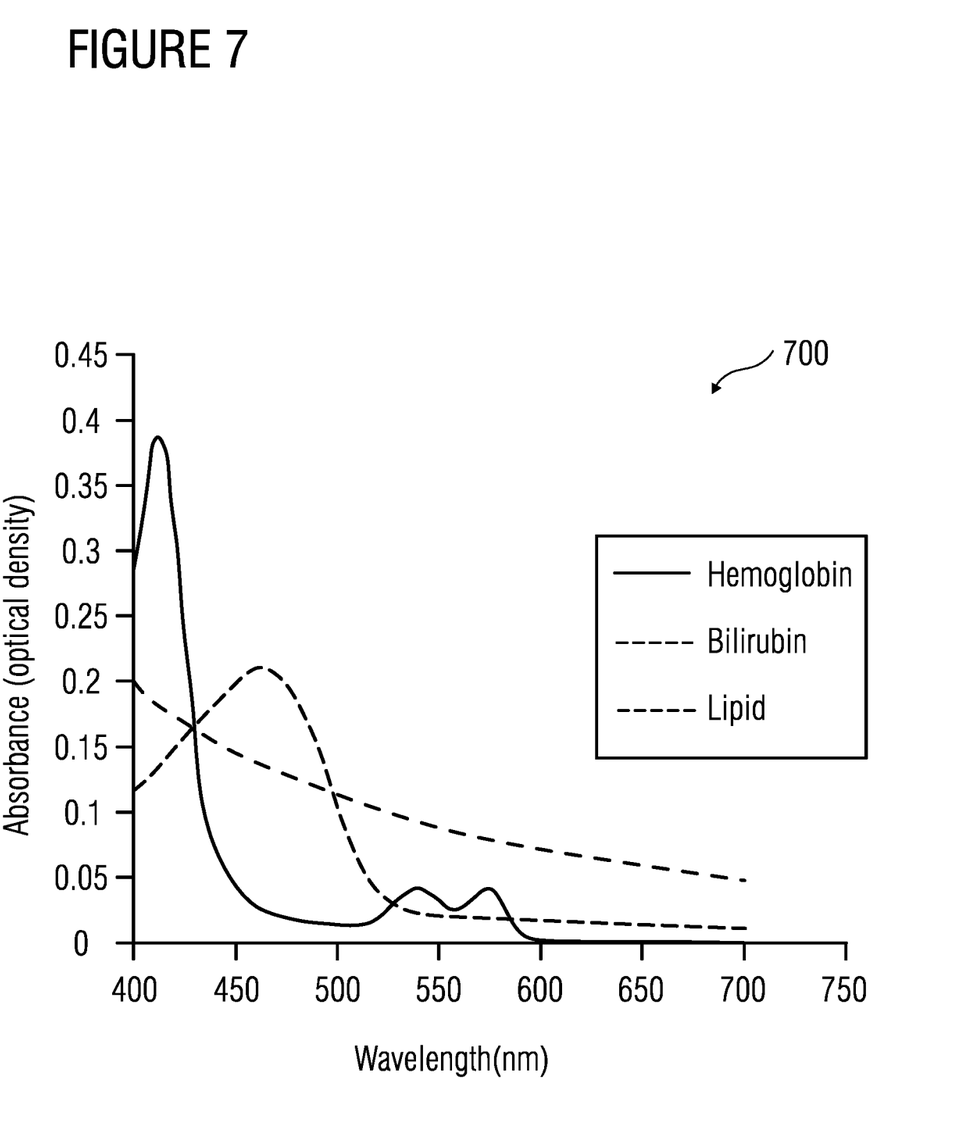
FIG. 7 illustrates an embodiment of an absorption spectrum of free-hemoglobin, bilirubin and lipids.

FIG. 4 illustrates a flowchart of an embodiment of a method 400 of determining the concentration of one or more analytes in the whole blood sample. At step 401, the whole blood sample is introduced through the channel 306. The whole blood sample may be introduced into the microfluidic channel 306 from one end of the channel 306. The whole blood sample may form a uniform layer in the channel 306. At step 402, a cell-free plasma layer is generated in the microfluidic channel 306. The cell-free plasma layer may be generated, for example, using acoustophoresis. Acoustophoresis is a method of causing particles exposed to an acoustic standing wave field to move in the sound field. Therefore, when the whole blood sample is exposed to an acoustic standing wave field, the blood cells migrate towards the sound field, thereby generating a cell-free plasma layer. Alternatively, the cell-free plasma layer may be generated by differential wetting in capillaries in the microfluidic channel 306. At step 403, the cell-free plasma layer may be illuminated with light having varying wavelengths. The light from the light source 301 may be directed to the microfluidic channel 306 such that the cell-free plasma layer is illuminated with the light. The light source 301 may be capable of emitting light at varying wavelengths. Therefore, based on the type of analyte to be determined, the cell-free plasma layer may be illuminated with light of varying wavelengths. In an embodiment, the cell-free plasma layer may be illuminated with light at wavelengths chosen from a range between 400 nm and 420 nm; 440 nm and 460 nm; and/or 520 nm and 650 nm. The wavelength of the light may be determined based on the absorption peak value associated with the one or more analytes to be determined. FIG. 7 illustrates an embodiment of an absorption spectrum 700 associated with free-hemoglobin, bilirubin and lipids. According to the absorption spectrum 700, maximum absorbance for free hemoglobin is achieved at a wavelength range of 400 nm to 420 nm. Similarly, the maximum absorbance for bilirubin is achieved at wavelength range of 440 nm to 460 nm. For lipids, the wavelength range of 520 nm to 650 nm is chosen such that there is minimum spectral interference from the other two analytes. Therefore, the wavelength range of 400 nm and 420 nm is associated with the analyte free hemoglobin; the wavelength range of 440 nm and 460 nm is associated with the analyte bilirubin and the wavelength range of 520 nm and 650 nm is associated with scattering of the analyte lipid.

At step 404 of the method 400, an image of the illuminated cell-free plasma layer in the channel 306 is obtained. In an embodiment, the image of the cell-free plasma layer may be captured using the image capturing module 303, 304. The image may therefore be received from the image capturing module 303, 304. Alternatively, the captured image may be stored in the calibration database 102 and may be obtained from the calibration database 102 for further analysis. Such image of the cell-free plasma layer may be obtained each time the plasma layer is illuminated with the chosen wavelength. Therefore, for example, if the cell-free plasma layer is illuminated with light having three different wavelengths, one image for each of the three wavelengths is obtained. At step 405, the obtained image is analyzed by the image processing module to determine the concentration of one or more analytes in the whole blood sample.

Figure 5:
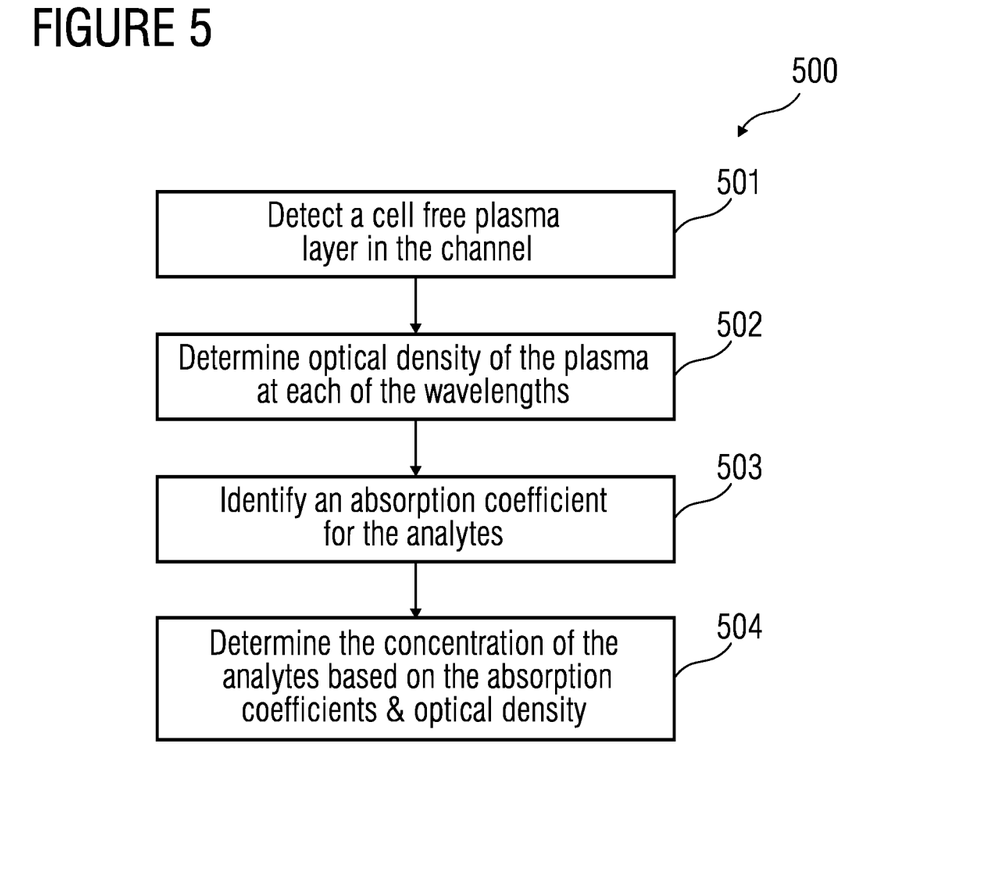
FIG. 5 illustrates a flowchart of an embodiment of a method of analyzing an image to determine the concentration of one or more analytes.
Figure 6:
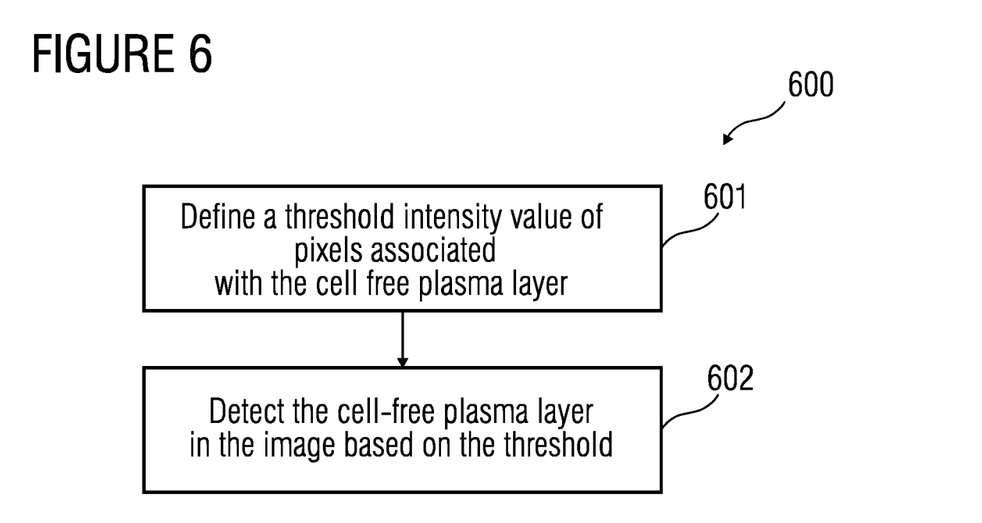
FIG. 6 illustrates a flowchart of an embodiment of a method of determining a cell-free plasma layer in an image.

FIG. 5 illustrates a flowchart of an embodiment of a method 500 of analyzing the image to determine the concentration of one or more analytes in the whole blood sample. At step 501, a cell-free plasma layer is detected in the image. The cell-free plasma layer may be detected in the image, for example, based on the pixel intensities. The method steps involved in detecting the cell-free plasma layer in the image is described in detail in FIG. 6. Referring to FIG. 6, a chart of an embodiment of a method 600 of determining a cell-free plasma layer in the image is illustrated. At step 601, a threshold associated with an intensity value of pixels of the cell-free plasma layer is determined. The pixels associated with the cell-free plasma layer may have a higher intensity pixel value in comparison to pixel value associated with the blood cells (predominantly red blood cells). Therefore, a threshold may be defined such that at step 602, the cell-free plasma layer may be detected in the image based on the threshold.

At step 502 of the method 500, an optical density associated with the plasma is determined at each of the chosen wavelengths. In an embodiment, the image processing module 105 may be calibrated with known standard samples of the analytes to be determined, before an unknown sample is tested. The calibration enables determination of absorption coefficient associated with each of the analytes to be determined. Therefore, known samples may be of free hemoglobin, bilirubin and lipid taken individually. Absorption coefficients for each analyte are constant and may depend on the material property of the analytes and the wavelength of illuminated light. In order to calibrate the image processing module 105, known standard samples of free hemoglobin, bilirubin and lipid are used at defined concentrations. The concentrations for free hemoglobin may be, for example, in the range between 0 mg/dL and 600 mg/dL. An image is obtained for concentrations of, for example, 50 mg/dL; 100 mg/dL; 200 mg/dL; and 400 mg/dL of free hemoglobin at each of the chosen wavelengths. Similarly, the concentrations for bilirubin may be, for example, in the range of 0 mg/dL to 50 mg/dL. An image is obtained for concentrations of, for example, 1.25 mg/dL; 2.5 mg/dL; 5 mg/dL; 10 mg/dL; 20 mg/dL; and 40 mg/dL of bilirubin at each of the chosen wavelengths. Known standard concentrations of lipid may range from 0 mg/dL to 800 mg/dL. An image is obtained for concentrations of, for example, 75 mg/dL; 150 mg/dL; 300 mg/dL and 600 mg/dL.

An optical density is calculated for each analyte, at each concentration. Optical density is a logarithmic ratio of falling radiation to the transmitted radiation through the sample. Optical density is a fraction of absorbed radiation at a particular wavelength. Optical density may be calculated using the following mathematical expression:

$$\text{Optical density} = -\log\frac{I}{I_0}$$

where I refers to mean pixel value of the sample and $I_0$ refers to mean pixel value of blank. Optical density may also be referred to as a product of absorption coefficient and concentration. Therefore, for a given analyte, the optical density may be depicted as:

Optical density=ε[C]

where ε is the absorption coefficient of the analyte and C is the concentration of the analyte. Therefore, for pure and known samples of free hemoglobin, bilirubin and lipids, the optical density may be calculated.

Figure 8:
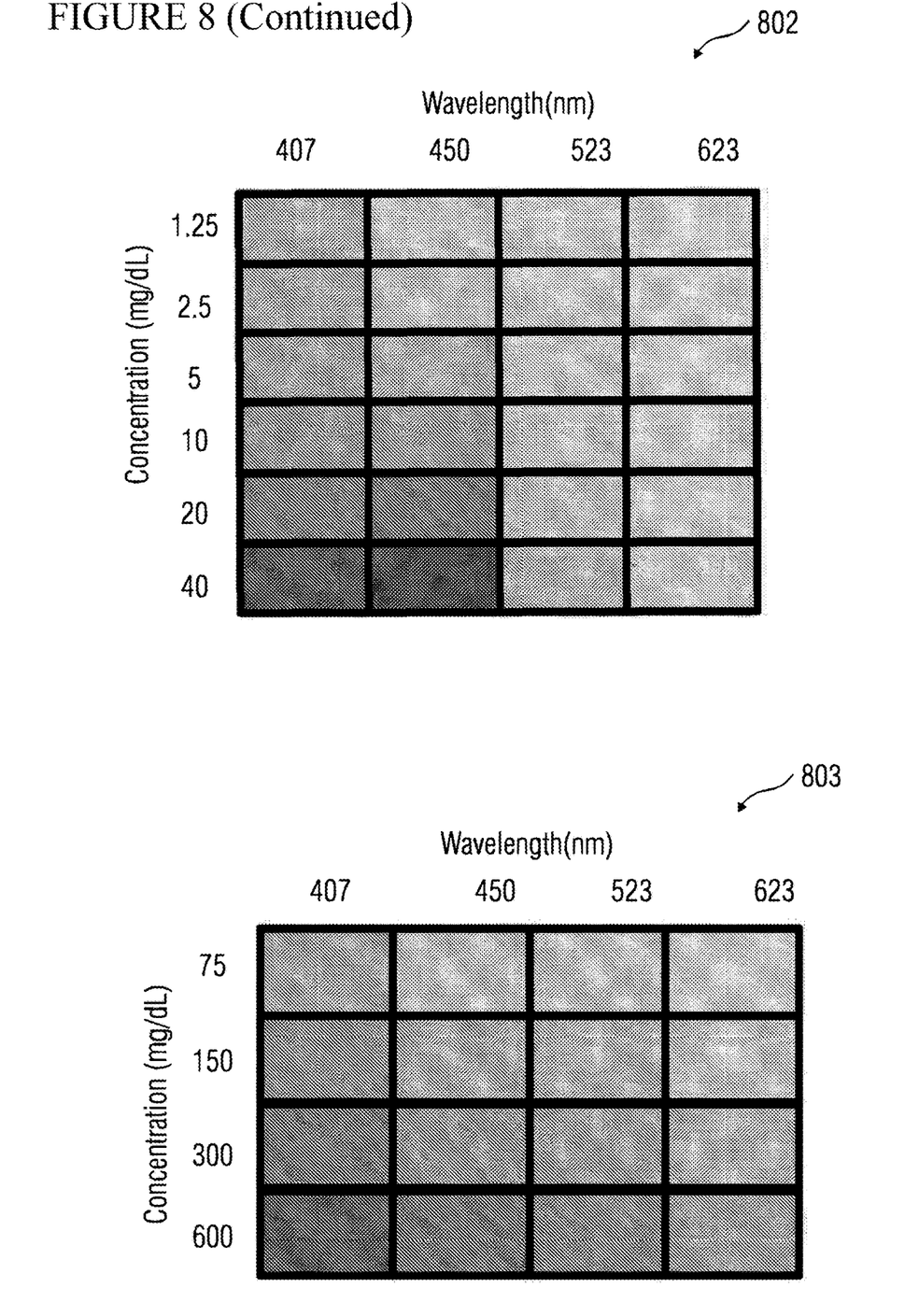
FIG. 8 illustrates an embodiment of a set of images obtained for each analyte of known concentrations, at varying wavelengths.

FIG. 8 illustrates an embodiment of a set of images 801, 802, 803 obtained for each analyte of known concentrations, at varying wavelengths. The set of images 801, 802, 803 may be the calibration dataset. The first set of images 801 is associated with free-hemoglobin. The images are obtained for free hemoglobin concentrations of 50 mg/dL; 100 mg/dL; 200 mg/dL and 400 mg/dL. The free hemoglobin sample at each of these concentrations is illuminated with light having a wavelength in the ranges of 400 nm to 420 nm; and/or 440 nm to 460 nm; and/or 520 nm to 650 nm. From the image set 801, it is observed that the absorption peak for free hemoglobin at each concentration is achieved at wavelength range of 400 nm to 420 nm. The second set of images 802 is associated with bilirubin. The images are obtained for bilirubin concentrations of 1.25 mg/dL; 2.5 mg/dL; 5 mg/dL; 10 mg/dL; 20 mg/dL; and 40 mg/dL. The bilirubin sample at each of these concentrations is illuminated with light having a wavelength in the ranges of 400 nm to 420 nm; and/or 440 nm to 460 nm; and/or 520 nm to 650 nm. From the image set 802, it is observed that the absorption peak for bilirubin at each concentration is achieved at wavelength range of 440 nm to 460 nm. The third set of images 803 is associated with lipids. The images are obtained for lipid concentrations of 75 mg/dL; 150 mg/dL; 300 mg/dL and 600 mg/dL. The lipid sample at each of these concentrations is illuminated with light having a wavelength in the ranges of 400 nm to 420 nm; and/or 440 nm to 460 nm; and/or 520 nm to 650 nm. From the image set 803, it is observed that lipids scattering of illuminated light at each concentration is achieved at wavelength range of 520 nm to 650 nm.

Figure 9:
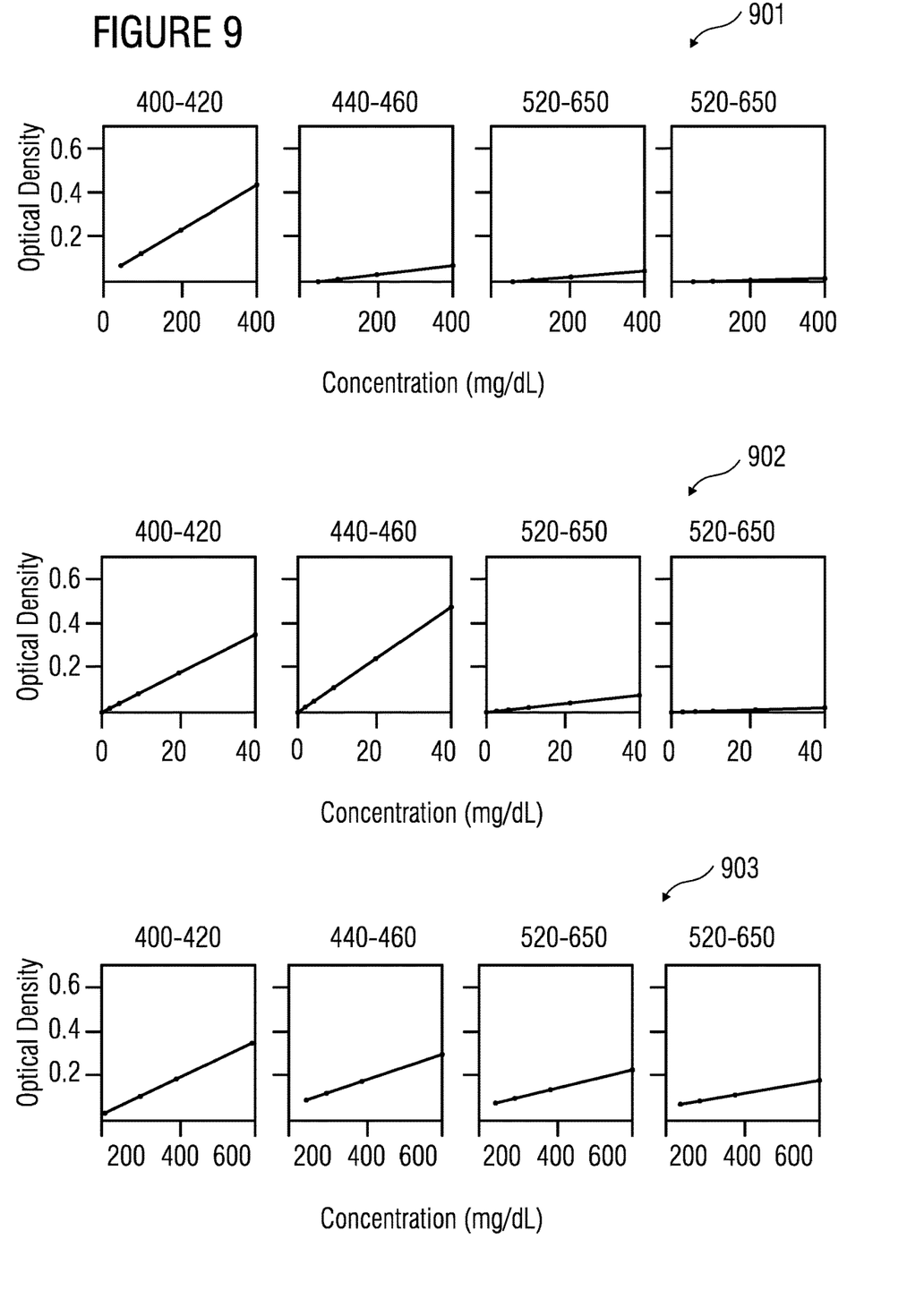
FIG. 9 illustrates an embodiment of a graphical representation obtained for the optical densities of free hemoglobin, bilirubin and lipids at known concentrations and at varying wavelengths.

FIG. 9 illustrates a set of graphical representations 901, 902, 903 obtained for the optical densities of free hemoglobin, bilirubin and lipids at known concentrations and at varying wavelengths. The graphical representation set 901 depicts that a gradient for absorption of light with respect to free hemoglobin concentration is steeper for wavelength range of 400 nm to 420 nm with respect to the other wavelength ranges. Similarly, the graphical representation set 902 for bilirubin depicts maximum optical density achievement at wavelength range of 440 nm to 460 nm. Additionally, the graphical representation set 903 depicts scattering of light due to lipids. The absorption coefficients for each of the analytes at each wavelength range may be derived from the graphical representations 901, 902, 903 and an absorption coefficient matrix may be computed.

$$\begin{bmatrix} C_{Hb} \\ C_{Bil} \\ C_{Lip} \end{bmatrix} = \begin{bmatrix} \varepsilon_{Hb}(\lambda_v) & \varepsilon_{Bil}(\lambda_v) & \varepsilon_{Lip}(\lambda_v) \\ \varepsilon_{Hb}(\lambda_b) & \varepsilon_{Bil}(\lambda_b) & \varepsilon_{Lip}(\lambda_b) \\ \varepsilon_{Hb}(\lambda_g) & \varepsilon_{Bil}(\lambda_g) & \varepsilon_{Lip}(\lambda_g) \end{bmatrix}^{-1} \begin{bmatrix} OD(\lambda_v) \\ OD(\lambda_b) \\ OD(\lambda_g) \end{bmatrix}$$

Figure 10:
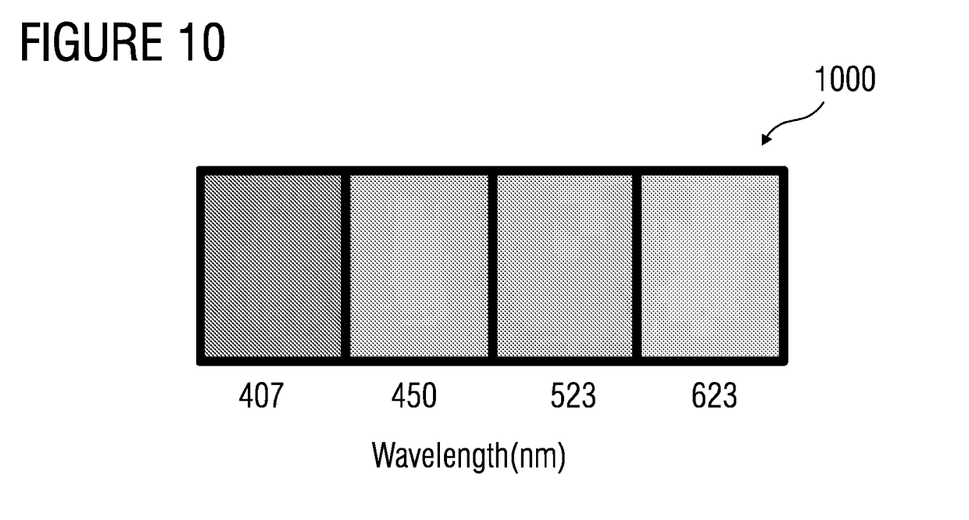
FIG. 10 illustrates an embodiment of a set of images obtained for an unknown sample at varying wavelengths.

In an embodiment, the image processing module 105 may be trained based on the images obtained for samples with known concentrations and the absorption coefficient matrix to accurately determine the concentration in an unknown sample. Therefore, when the whole blood sample, containing the analytes in unknown concentrations is analyzed, at step 502 of method 500, the obtained images are analyzed to determine the optical density of the analytes. FIG. 10 illustrates an embodiment of images 1000 obtained for the cell-free plasma layer at wavelength ranges of 400 nm to 420 nm; and/or 440 nm to 460 nm; and/or 520 nm to 650 nm. At step 503, the absorption coefficient of each analyte is determined at each of the varying wavelengths. The absorption coefficient matrix derived from the known samples is used to determine the concentration of the analytes in the whole blood sample, at step 504.

Figure 11:
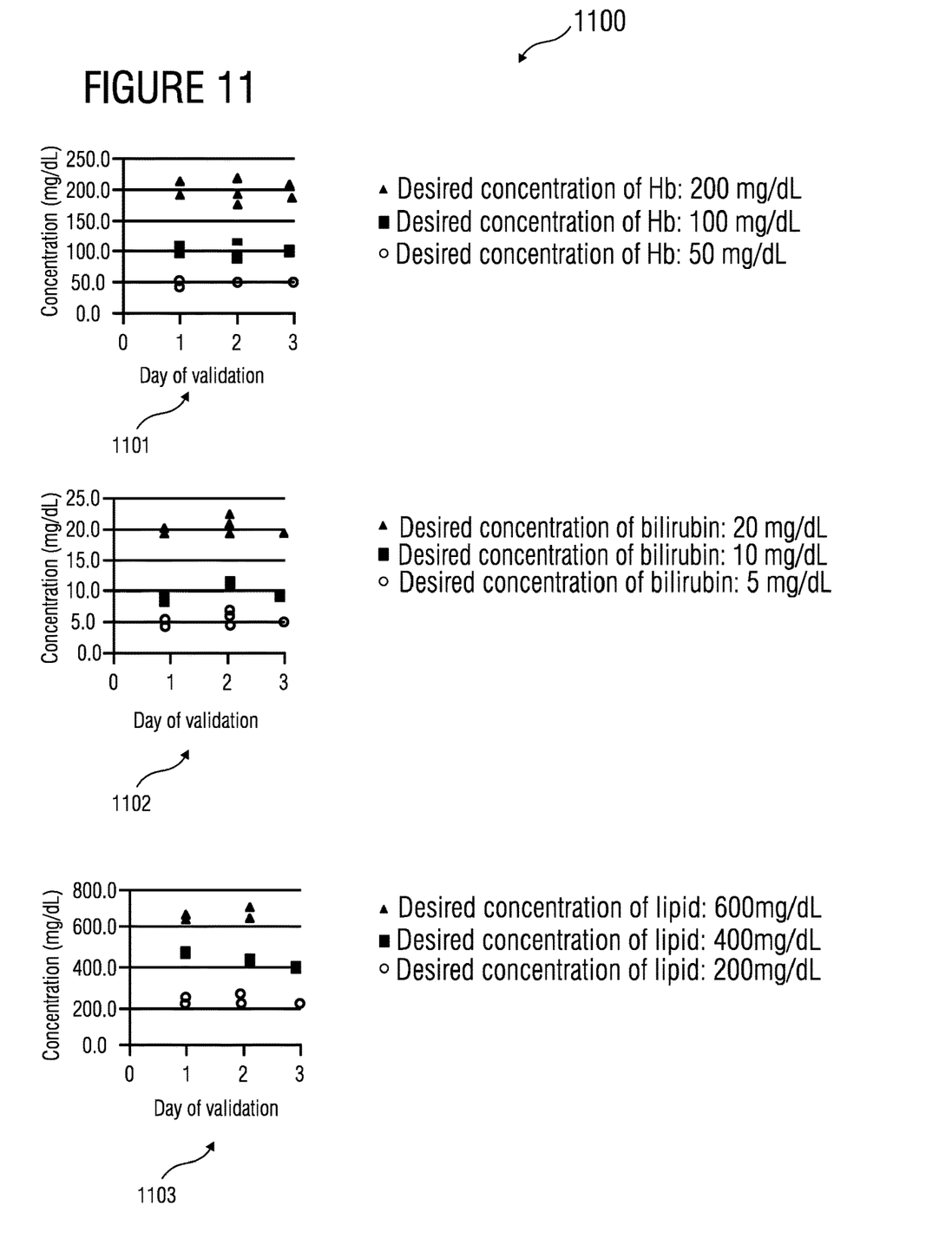
FIG. 11 illustrates an embodiment of graphical representations 1100 depicting the consistency of the invention in determining concentrations of one or more analytes in known samples.

FIG. 11 illustrates an embodiment of graphical representations 1100 depicting the consistency of the invention in determining concentrations of one or more analytes in known samples. The graphical representation 1101 refers to analysis results of free hemoglobin sample at known concentrations of 50 mg/dL, 100 mg/dL and 200 mg/dL. The standard deviation of test results is as below:

| Desired concentration (mg/dL) | 50 | 100 | 200 |
|---|---|---|---|
| Mean of determined concentration (mg/dL) | 47.0 | 100.3 | 198.0 |
| Standard deviation | 3.3 | 10.2 | 14.7 |
| Coefficient of variation (%) | 7.0 | 10.2 | 7.4 |

The graphical representation 1102 refers to analysis results of bilirubin sample at known concentrations of 5 mg/dL, 10 mg/dL and 20 mg/dL. The standard deviation of test results as below:

| Desired concentration (mg/dL) | 5 | 10 | 20 |
|---|---|---|---|
| Mean of determined concentration (mg/dL) | 5 | 9.8 | 19.8 |
| Standard deviation | 0.8 | 1.4 | 1.1 |
| Coefficient of variation (%) | 7.0 | 10.2 | 7.4 |

The graphical representation 1103 refers to analysis results of lipid sample at known concentrations of 200 mg/dL, 400 mg/dL and 600 mg/dL. The standard deviation of test results as below:

| Desired concentration (mg/dL) | 200 | 400 | 600 |
|---|---|---|---|
| Mean of determined concentration (mg/dL) | 243.7 | 470.4 | 665.9 |
| Standard deviation | 22.5 | 16.0 | 45.4 |
| Coefficient of variation (%) | 9.2 | 3.4 | 6.8 |

Since the image data set 1000 have several thousand pixels, the mean values of pixels do not significantly affect the results. Even in the presence of stray red blood cells, the invention provides desired results. As only a small area of the obtained image is analyzed to determine the concentration of analytes, low sample volumes of <1 microliter is sufficient for optical analysis. Furthermore, the invention is cost effective as the hardware components are limited. Additionally, the channel 306 is reusable. The invention also enables detection of bilirubin and lipids in the sample along with hemolysis measurement.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials, and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

What is claimed is:

1. A method of determining a free hemoglobin concentration, a bilirubin concentration, and a lipid concentration in a whole blood sample, the method comprising:
   introducing the whole blood sample through a microfluidic channel;
   generating a cell-free plasma layer in the microfluidic channel using acoustophoresis;
   illuminating the cell-free plasma layer with light at three wavelengths or wavelength ranges, wherein a first wavelength/wavelength range is in a range of from 400 nm to 420 nm, a second wavelength/wavelength range is in a range of from 440 nm to 460 nm, and a third wavelength/wavelength range is in a range of from 520 nm to 650 nm;
   obtaining a first monochromatic image of the illuminated cell-free plasma layer at the first wavelength/wavelength range, obtaining a second monochromatic image of the illuminated cell-free plasma layer at the second wavelength/wavelength range, and obtaining a third monochromatic image of the illuminated cell-free plasma layer at the third wavelength/wavelength range; and
   analyzing the first, second, and third images to determine the concentration of free hemoglobin based on the first image, the concentration of bilirubin based on the second image, and the concentration of lipid based on the third image, and wherein analyzing the first, second, and third images comprises:
   detecting a cell-free plasma layer in the first, second, and third images, wherein the detection comprises defining a threshold of intensity value of pixels associated with the cell-free plasma layer and detecting the cell-free plasma layer in each image based on the threshold;
   determining an optical density of the plasma at the first wavelength/wavelength range for the first image, the second wavelength/wavelength range for the second image, and the third wavelength/wavelength range for the third image;
   identifying an absorption coefficient for free hemoglobin for the first image, bilirubin for the second image, and lipid for the third image; and
   determining the concentration of free hemoglobin based on the optical density and the absorption coefficient for the first image;
   determining the concentration of bilirubin based on the optical density and the absorption coefficient for the second image; and
   determining the concentration of lipid based on the optical density and the absorption coefficient for the third image.

2. The method according to claim 1, wherein a depth of the microfluidic channel is in the range between 100 and 200 μm.

3. A system for determining a concentration of free hemoglobin, bilirubin, and lipid in a whole blood sample, the system comprising:
   a processing unit;
   a calibration database coupled to the processing unit;
   a memory coupled to the processing unit, the memory comprising an image processing module configured for performing the obtaining and analyzing steps of the method of claim 1, wherein in the step detecting a cell-free plasma layer in the image, the image processing module is configured to define a threshold of intensity value of pixels associated with the cell-free plasma layer and detect the cell-free plasma layer in the image based on the threshold.

4. The system according to claim 3, wherein in analyzing the image, the image processing module is configured to:
   determine an optical density of the plasma at each of the varying wavelengths;
   identify an absorption coefficient for the one or more analytes; and
   determine the concentration of the one or more analytes based on the optical density and the absorption coefficient.

5. A device for determining a concentration of free hemoglobin, bilirubin, and lipid in a whole blood sample, the device comprising:
   a microfluidic channel configured to carry the whole blood sample, and wherein a cell-free plasma layer is generated from the whole blood sample within the microfluidic channel using acoustophoresis;
   a light source configured to emit light at three wavelengths or wavelength ranges, wherein the cell-free plasma layer is illuminated at a first wavelength/wavelength range in a range of from 400 nm to 420 nm, a second wavelength/wavelength range in a range of from 440 nm to 460 nm, and a third wavelength/wavelength range in a range of from 520 nm to 650 nm using the light source;
   an image capturing module configured to capture a pixel-based monochromatic image of the illuminated cell-free plasma layer at each of the first, second, and third wavelengths/wavelength ranges, wherein the image capturing module comprises one or more lenses and an imaging sensor, wherein the imaging sensor is a charge-coupled device or complementary metal oxide semiconductor; and
   an image processing module configured for:
      determining an optical density of the plasma at the first wavelength/wavelength range for the first image, the second wavelength/wavelength range for the second image, and the third wavelength/wavelength range for the third image;
      identifying an absorption coefficient for free hemoglobin for the first image, bilirubin for the second image, and lipid for the third image; and
      determining the concentration of free hemoglobin based on the optical density and the absorption coefficient for the first image;
      determining the concentration of bilirubin based on the optical density and the absorption coefficient for the second image; and
      determining the concentration of lipid based on the optical density and the absorption coefficient for the third image.

6. The device according to claim 5, wherein a depth of the microfluidic channel is in the range between 100 and 200 µm.

* * * * *